US009855071B2

United States Patent
Shaltis (10) Patent No.: US 9,855,071 B2
(45) Date of Patent: Jan. 2, 2018

(54) THROMBECTOMY CATHETER SYSTEM WITH REFERENCE MEMBER

(71) Applicant: Covidien LP, Mansfield, MA (US)

(72) Inventor: Phillip Shaltis, Sharon, MA (US)

(73) Assignee: Covidien LP, Mansfield, MA (US)

( * ) Notice: Subject to any disclaimer, the term of this patent is extended or adjusted under 35 U.S.C. 154(b) by 389 days.

(21) Appl. No.: 14/170,935

(22) Filed: Feb. 3, 2014

(65) Prior Publication Data
US 2015/0216650 A1    Aug. 6, 2015

(51) Int. Cl.
*A61B 17/22* (2006.01)
*A61D 1/02* (2006.01)
*A61B 17/3207* (2006.01)
*A61B 90/00* (2016.01)

(52) U.S. Cl.
CPC .. *A61B 17/320758* (2013.01); *A61B 17/3207* (2013.01); *A61B 2017/22079* (2013.01); *A61B 2017/22084* (2013.01); *A61B 2017/22094* (2013.01); *A61B 2090/063* (2016.02); *A61B 2090/3966* (2016.02)

(58) Field of Classification Search
CPC ........ A61B 17/3207; A61B 17/320758; A61B 2017/22081; A61B 2017/22084; A61B 2017/22094; A61B 17/32037; A61B 17/32075; A61B 2017/320716; A61B 2017/22001; A61B 17/22079
See application file for complete search history.

(56) References Cited

U.S. PATENT DOCUMENTS

| 5,011,488 | A | * | 4/1991 | Ginsburg | A61B 17/22 604/104 |
|---|---|---|---|---|---|
| 5,947,985 | A | * | 9/1999 | Imran | A61B 17/32037 604/101.05 |
| 6,497,711 | B1 | * | 12/2002 | Plaia | A61B 17/32072 606/159 |
| 6,652,548 | B2 | | 11/2003 | Evans et al. | |
| 7,833,240 | B2 | * | 11/2010 | Okushi | A61B 17/32072 606/159 |
| 8,162,878 | B2 | | 4/2012 | Bonnette et al. | |
| 2008/0183197 | A1 | * | 7/2008 | Sepetka, IV | A61B 17/22031 606/159 |
| 2009/0093791 | A1 | * | 4/2009 | Heuser | A61B 17/12136 604/509 |
| 2010/0023033 | A1 | | 1/2010 | Mauch et al. | |

(Continued)

*Primary Examiner* — Melanie Tyson (57) ABSTRACT

A surgical apparatus includes an elongate outer sheath dimensioned for positioning within a body lumen of a patient, a reference member and a removal device. The reference member is adapted for longitudinal movement relative to the elongate outer sheath between a first position at least partially disposed within a longitudinal lumen of the outer sheath and a second position at least partially exposed from the longitudinal lumen. The reference member is adapted to expand when in the second position to generally conform to an internal dimension of the body lumen. The reference member includes a radiopaque material for visualizing the reference member to assist in determining physical characteristics of the body lumen when in the second position. The removal device is adapted for longitudinal movement relative to the reference member, and is configured for disrupting at least a portion of the occlusion within the body lumen.

21 Claims, 10 Drawing Sheets

(56) References Cited

U.S. PATENT DOCUMENTS

| | | | |
|---|---|---|---|
| 2010/0036312 A1* | 2/2010 | Krolik | A61B 17/221 604/22 |
| 2010/0137892 A1* | 6/2010 | Krolik | A61B 17/221 606/159 |
| 2011/0022038 A1* | 1/2011 | Seshadri | A61B 17/3207 606/7 |
| 2011/0034937 A1* | 2/2011 | Mustapha | A61B 17/22 606/127 |
| 2013/0103062 A1 | 4/2013 | To et al. | |
| 2014/0155908 A1* | 6/2014 | Rosenbluth | A61B 17/32072 606/127 |

* cited by examiner

THROMBECTOMY CATHETER SYSTEM WITH REFERENCE MEMBER

TECHNICAL FIELD

The present disclosure relates to a thrombectomy catheter system, and, more particularly, relates to a thrombectomy catheter system with a reference member.

BACKGROUND

Devices for removing occlusions from a body lumen, such as a vasculature of a patient, to reestablish patency of the body lumen are well known in the art. These devices may be of the mechanical, electrical or chemical type. Each type of device may be suited for removal of a particular type of occlusive material from the body lumen, such as chronic clots, sub-acute clots or acute clots.

One issue associated with these devices is the ability to effectively and reliably view the internal wall or boundary of the body lumen to assist in removal of the occlusion while at the same time minimizing the likelihood of causing damage to the body lumen. Another issue is determining the extent or progress of removal of the occlusion during the procedure. Typically, a contrast agent is injected into the vasculature to image a vessel under fluoroscopy, but large quantities of contrast may be needed for a longer procedure, which may be harmful and/or contraindicated for many patients. Thus, a method of visualizing the vasculature under simple x-ray without the use of contrast agents is desirable.

SUMMARY

Accordingly, a thrombectomy catheter system capable of defining the internal wall of the boundary and providing a reference during removal of the occlusion, such as by maceration, cutting, or chemical removal, is disclosed. In general, in one aspect, the implementation of the disclosure features a surgical apparatus including an elongate outer sheath dimensioned for positioning within a body lumen of a patient adjacent an occlusion, a reference member, and a removal device. The elongate outer sheath has a proximal end and a distal end and a longitudinal axis extending between the proximal end and the distal end, and defines a longitudinal lumen along at least a portion of the longitudinal axis. The reference member is adapted for longitudinal movement relative to the elongate outer sheath between a first position at least partially disposed within the longitudinal lumen and a second position at least partially exposed from the longitudinal lumen. The reference member is adapted to expand when in the second position to generally conform to an internal dimension of the body lumen. The reference member includes a radiopaque material for visualizing the reference member to assist in determining physical characteristics of the body lumen when in the second position. The removal device is positioned with respect to the elongate outer sheath, and is adapted for longitudinal movement relative to the reference member. The removal device is configured to disrupt at least a portion of the occlusion within the body lumen.

In embodiments, the radiopaque material defines radiopaque markers arranged in predefined radial and longitudinal spaced relation.

In some embodiments, the reference member is dimensioned for positioning at least partially within the occlusion within the body lumen.

In embodiments, the reference member is adapted for reciprocal longitudinal movement relative to the outer sheath between the first and second positions, and is repositionable to the first position subsequent to movement thereof to the second position.

In other embodiments, the reference member is configured to assist in centering the removal device within the body lumen.

The reference member may include a self-expanding coil, a self-expanding mesh or cage, self-expanding fingers, or a balloon.

In embodiments, the reference member includes cutting edges configured to cut at least a portion of the occlusion.

In some embodiments, the removal device is adapted for reciprocal longitudinal movement relative to the reference member between a retracted position disposed within the reference member and an advanced position distal of the reference member.

In general, in another aspect, the implementation of the disclosure features a surgical apparatus including an elongate outer sheath dimensioned for positioning within a vasculature of a patient, a reference member and a removal device. The elongate outer sheath has a proximal end and a distal end and a longitudinal axis extending between the proximal end and the distal end, and defines a longitudinal lumen along at least a portion of the longitudinal axis. The outer sheath is advanceable to a location adjacent an occlusion in the vasculature. The reference member is adapted for longitudinal movement relative to the elongate outer sheath between a first position at least partially disposed within the longitudinal lumen and a second position at least partially exposed from the longitudinal lumen. The reference member is dimensioned for at least partial insertion within the occlusion and capable of generally conforming to internal boundaries of the occlusion and areas of the vasculature adjacent the occlusion. The reference member further includes a radiopaque material for visualizing the reference member to assist in determining characteristics of at least one of the occlusion and the areas of the vasculature adjacent the occlusion. The removal device is positioned with respect to the elongate outer sheath, and is adapted for longitudinal movement relative to the reference member. The removal device is configured to disrupt at least a portion of the occlusion within the vasculature.

In another embodiment, a surgical method is disclosed. The surgical method includes:
advancing an elongate outer sheath within a body lumen to a location adjacent an occlusion;
deploying a reference member including radiopaque material from the elongate outer sheath;
expanding the reference member whereby the reference member is at least partially disposed within the occlusion;
visualizing the reference member to ascertain physical characteristics of at least one of the occlusion and the areas of the body lumen adjacent the occlusion;
advancing a removal device relative to the elongate outer sheath; and
activating the removal device to disrupt at least a portion of the occlusion.

In an embodiment, visualizing the reference member is performed prior to activating the removal device. Visualizing the reference member also may be performed subsequent to activating the removal device to determine progress of the disruption of the occlusion.

In embodiments, the reference member includes radiopaque markers arranged in predefined radial and longitudinal spaced relation and wherein visualizing the reference member includes viewing the radiopaque markers, such as by x-ray, to determine the physical characteristics of the occlusion.

In some embodiments, the method further includes retracting the reference member from the occlusion prior to activating the removal device.

In embodiments, the method includes advancing the reference member within the occlusion subsequent to activating the removal device, and thereafter visualizing the reference member to ascertain progress of disrupting the occlusion.

In other embodiments, the method further includes: retracting the reference member from the occlusion;
advancing the removal device relative to the reference member; and
removing additional portions of the occlusion with the removal device.

Embodiments can include one or more of the following advantages.

The thrombectomy catheter system facilitates removal of occlusive materials including, e.g., acute or chronic clots, from a body lumen while minimizing the potential risk of causing incidental damage to the surrounding healthy tissue. The thrombectomy catheter system includes a reference member which provides a visual indication of the body lumen, such as a vasculature, and also assists in determining the extent of progress of removal of occlusive material. Moreover, the reference member will provide a clear definition of the inner boundary of the body lumen including both open and partially occluded inner boundaries of the body lumen, assisting placement of the removal device of the system relative to the occlusion and/or providing quantitative data with respect to the body lumen dimensions and/or dimensions associated with the occlusion.

The thrombectomy catheter system is self-contained, incorporating the components required to initiate and complete the thrombectomy procedure. Specifically, the reference member and removal device are incorporated within the outer sheath of the system and move relative to each other to perform the respective referencing or disrupting functions for occlusion removal, without requiring removal and/or introduction of supplemental instrumentation, while also providing real time status of the progress of occlusion removal.

Other aspects, features, and advantages will be apparent from the description, drawings, and the claims. While the thrombectomy catheter is described as being deployed in the vasculature of a patient (e.g., arteries and veins), the thrombectomy catheter can be used in other body lumens, including, but not limited to, the urinary tract, fallopian tubes, vas deferens, grafts, and fistulas.

DETAILED DESCRIPTION

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician. As used herein, the term "subject" refers to a human patient or other animal. The term "lumen" refers to any lumen within the body, either natural or artificial, such as, for example, blood vessels, blood vessel grafts, fistulas, and the like. As used herein, the term "occlusion" or "occlusive material" refers to any partial or total blockage of a lumen, such as, for example, thrombus, atheromas, plaque, tumors, cysts, clots and the like. The term "disrupt" refers to cutting, emulsing, coring, crushing, shredding, separating, disintegrating, breaking-up, rupturing, removing and the like.

Figure 1:
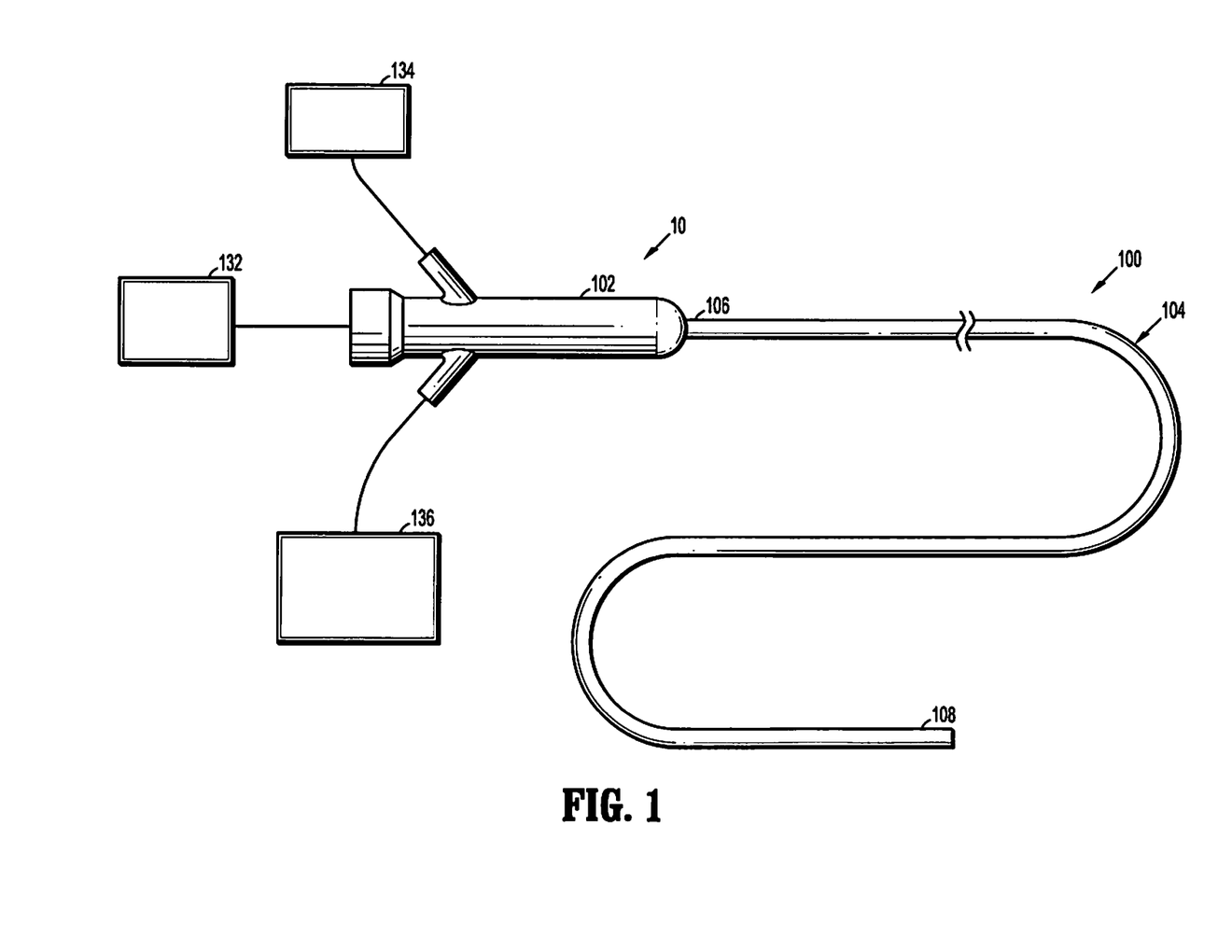
FIG. 1 is a plan view of a thrombectomy catheter system of the present disclosure illustrating a thrombectomy catheter, a drive mechanism, and vacuum and fluid sources in communication with the thrombectomy catheter.

With reference to FIG. 1, a thrombectomy catheter system 10 in accordance with the present disclosure is illustrated. The catheter system 10 includes a thrombectomy catheter 100 having a handle 102 and an elongated catheter body 104 extending from the handle 102. The handle 102 may be dimensioned for engagement by the user or may be dimensioned for positioning on a support surface. The handle 102 may include any number and/or types of knobs, switches, buttons, etc. that are manually and/or autonomously operable to operate the catheter system 10.

Figure 2:
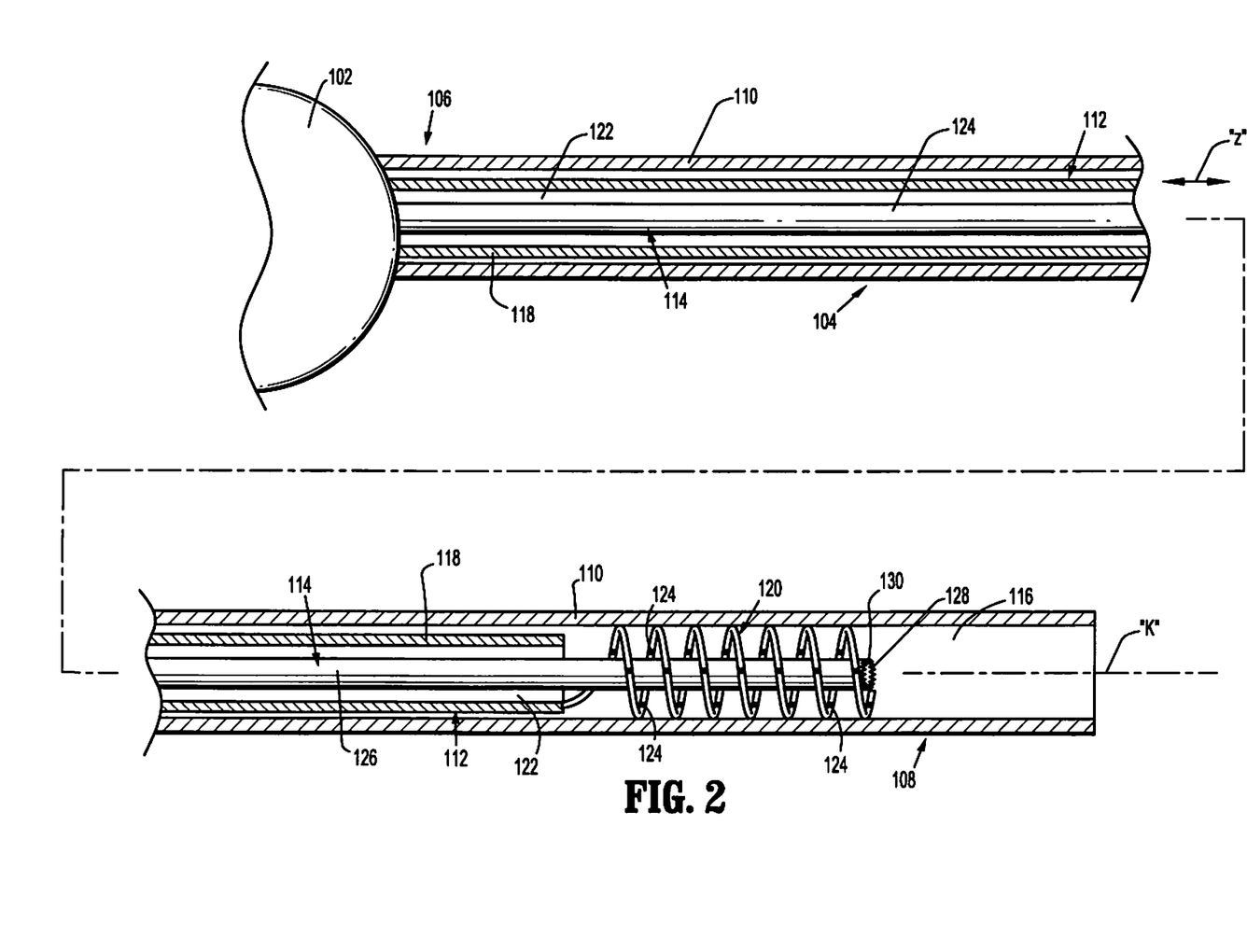
FIG. 2 is a side view in partial cross-section of the thrombectomy catheter of FIG. 1 illustrating an outer sheath, a reference member, and a removal device.
Figure 3:
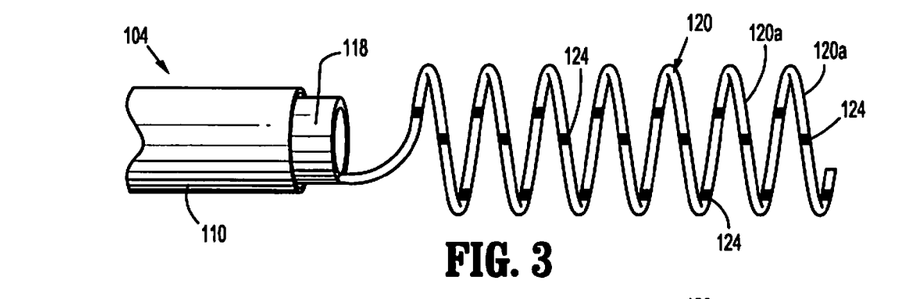
FIG. 3 is a side plan view of a distal end of the thrombectomy catheter of FIG. 2 illustrating the reference member in an at least partially exposed condition relative to the outer sheath.

With reference to FIGS. 1-3, the catheter body 104 includes an elongate outer sheath 110 that has a proximal end 106 and a distal end 108, and a longitudinal axis "k" (FIG. 2) extending between the proximal and distal ends 106, 108. As best depicted in FIG. 2, the catheter body 104 includes the outer sheath 110, a reference implement 112 and a removal device 114 each of which are at least partially disposed within the outer sheath 110. The outer sheath 110 defines a longitudinal lumen 116 therethrough at least along a portion of the longitudinal axis "k". The outer sheath 110 may be any suitable tube member fabricated from a material including, but not limited to, polymeric materials, elastomeric materials, for example, silicone and fabric materials, or a synthetic resin, for example, polyurethane, polyethylene, polypropylene, nylons, polytetrafluoroethylene (PTFE), polyether ether ketone (PEEK), PEBAX®, or polyimide. The outer sheath 110 may be reinforced with braids or coils, and the distal end 108 may be pre-curved, flexible, and/or deflectable.

The reference implement 112 includes a reference shaft 118 and a reference member 120 connected to the distal end of the reference shaft 118. The reference shaft 118 may define a longitudinal lumen 122 for reception and passage of the removal device 114. Alternatively, the reference shaft 118 may be a solid shaft extending parallel to the removal device 114 through the longitudinal lumen 116 of the outer sheath 110. The reference implement 112 is adapted for reciprocal longitudinal movement (depicted by directional arrows "z") within the lumen 116 of the outer sheath 110 between a first position in which the reference member 120 is at least partially confined within the outer sheath 110 (FIG. 2) and a second position in which the reference member 120 is at least partially exposed from the outer sheath 110 (FIG. 3). Any mechanism for causing relative movement of the reference implement 112 within the outer sheath 110 is envisioned including, e.g., with the use of slides, knobs, control dials or the like associated with the handle and coupled to the reference shaft 118.

Figure 4:
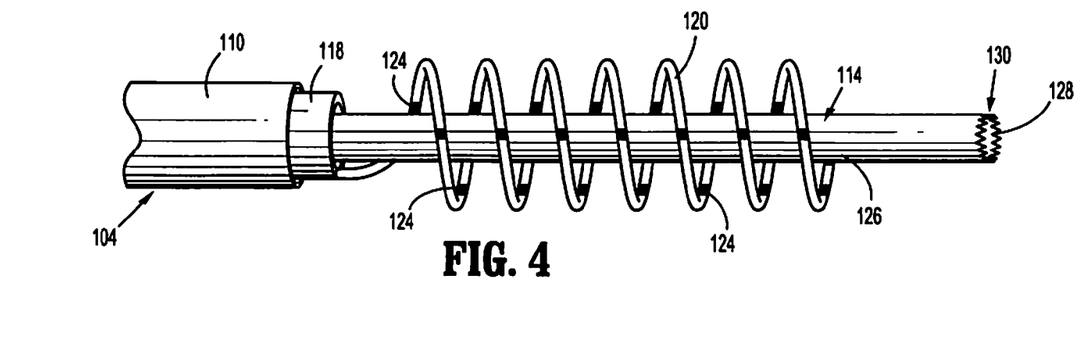
FIG. 4 is a side plan view of the distal end of the thrombectomy catheter of FIG. 2 illustrating the removal device extending through the reference member.

The reference member 120 may be an expandable coil, ribbon, cage, mesh or other suitable arrangement adapted to expand into engagement with an inner wall of the vasculature and/or occlusion. The reference member 120 may be self-expanding being formed, at least in part, of a self-expanding, shape-memory or super-elastic metal such as spring steel, nitinol, cobalt-chromium alloy or the like, and configured to be recaptured. Alternatively, the reference member 120 may be a biocompatible polymer with radiopaque markers disposed thereon. In the embodiment of FIGS. 2 thru 4, the reference member 120 is a self expanding coil. The coil is configured to transition from a constrained condition when positioned within the outer sheath 110 as depicted in FIG. 2 to an expanded condition when deployed from the outer sheath 110 as depicted in FIG. 3, and then back into a constrained condition when recaptured by the outer sheath 110. In the constrained condition, the reference member 120 may be substantially linear or define a compressed coil orientation. The constrained condition of the reference member 120 corresponds to the first position of the reference member 120 relative to the outer sheath 110 and the expanded condition of the reference member 120 corresponds to the second position of the reference member 120 relative to the outer sheath 110.

In the expanded condition, the reference member 120 provides a plurality of revolutions, loops or coil segments, which engage and conform to the inner wall of the vasculature. The reference member 120 may be fabricated, at least in part, from a radiopaque material, and thus will provide a clear definition of the inner wall or boundaries of the vasculature in which it is inserted when subjected to imaging, such as x-ray imaging.

Figure 3A:
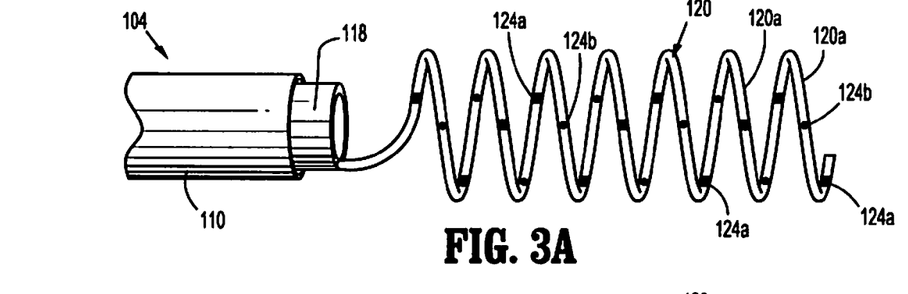
FIG. 3A is a side plan view of a distal end of another illustrative example of the reference member of FIG. 2 illustrating the reference member in an at least partially exposed condition relative to the outer sheath.

In the alternative, or additionally, the reference member 120 may include a plurality of distinct radiopaque markers 124 which are spaced at predetermined positions, including relative radial and longitudinal positions, on the reference member 120. Such markers 124 may be any shape, such as various symbols, geometrical shapes, numerals or the like. In preferred embodiments, the radiopaque markers 124 are bands circumferentially disposed around sections of the reference member 120, and equidistally spaced with respect to each other; however, any spacing of adjacent radiopaque markers 124 is suitable as long as the distances are known. In other preferred embodiments, the radiopaque markers 124 may be a combination of shapes at known spacing. For example, as shown in FIG. 3A, the radiopaque markers 124 may alternate between circumferential bands 124A and dots 124B. Such an alternating arrangement may aide the physician in determining the three dimensional shape while viewing a two-dimensional x-ray image. For example, by knowing the orientation, a physician may be able to infer that the circumferential bands 124A are further away than the dots 124B, and thus on one side of the vasculature as compared to the dots 124B, which may help provide a better picture of the vasculature. In embodiments, the radiopaque markers 124 may incorporate a material which is more radiopaque than the material from which the reference member 120 is fabricated.

The reference member 120, with or without the radiopaque markers 124, will 1) provide a clear visual definition of the inner boundary of the vasculature including both open and partially occluded (e.g., in the presence of an occlusion) inner boundaries of the vasculature; 2) assist in determining the location of the reference member 120 with respect to the occlusion; and 3) assist in providing quantitative data with respect to vascular dimensions and/or dimensions associated with the occlusion. The reference member 120 may also include sharpened edges 120a or similar surfaces, which may assist in disrupting or breaking up the occlusion.

With specific reference to FIG. 2, the removal device 114 may include a drive shaft 126 defining a lumen 128 and a leading cutting member 130 at the distal end of the drive shaft 126. The cutting member 130 may be any type of cutting device that can resect, cut, or otherwise disrupt the occlusion. For example, as depicted in the figures, the cutting member 130 may be at least partially annular in configuration, or in some embodiments, completely annular. The cutting member 130 is configured to disrupt occlusive material within a lumen upon movement of the drive shaft 126, such as by rotational and/or longitudinal movement. In embodiments, the cutting member 130 can include any suitable cutting arrangement that is configured to disrupt occlusive material. For example, the cutting member 130 can include any number of teeth, serrations, steps, blades, ridges, edges, or the like, and can have any suitable geometry and/or dimension for disrupting occlusive material. In other embodiments, the removal device 114 may be an electrosurgical device, a chemical delivery device, or a combination of each of these removal devices. For example, in removing an occlusion overnight with a tPA drip, the removal device 114 may be a simple drip catheter, and the reference member 120 provides a view of the progress of the occlusion removal under x-ray without needing to continually provide contrast to the patient over the course of several hours, or potentially a day.

The removal device 114 is adapted for longitudinal movement within the outer sheath 110 between a retracted position where the cutting member 130 is at least partially enclosed within the outer sheath 110 (FIG. 2), and an extended position where the cutting member 130 is at least partially exposed from the outer sheath 110 (FIG. 4). The removal device 114 is also adapted for longitudinal movement relative to the reference shaft 118 of the reference implement 112. For example, the removal device 114 may move within the reference shaft 118 if the reference shaft 118 is hollow, or alongside of the reference shaft 118 if the reference shaft 118 is solid. Any of the aforementioned mechanisms for causing relative movement of the removal device 114 to the reference shaft 118 are envisioned including, e.g., the use of slides, knobs, control dials or the like associated with the handle 102 and coupled to the removal device 114. Alternatively, each component may be manually moved relative to each other by having a proximal end of each extending out of the outer sheath 110.

The thrombectomy catheter system 10 may include any other devices necessary to operate the various components of the system. For example, with reference again to FIG. 1, the thrombectomy catheter system 10 may further include a drive mechanism depicted schematically as reference numeral 132. The drive mechanism 132, which can include any suitable mechanical and/or electrical component, may be coupled to and activate, either, or both, the removal device 114 and/or the reference implement 112. The drive mechanism 132 may impart the appropriate movement to the removal device 114, including, for example, rotational, oscillating, and/or vibrational movement. In embodiments, the drive mechanism 132 may impart similar movement to the reference implement 112 including the reference member 120. As a further alternative, the drive mechanism 132 may cause longitudinal movement of the removal device 114 and/or the reference implement 112 relative to the longitudinal axis "k" and the outer sheath 110. Any suitable electro-mechanical systems and/or gearing mechanisms may be incorporated into the drive mechanism 132 to effect the aforedescribed movements of the removal device 114 and/or reference implement 112.

The thrombectomy catheter system 10 also may include a vacuum source 134 and/or a fluid source 136, each being couplable to the handle 102 and in fluid communication with the catheter body 104. The vacuum source 134 may communicate negative pressure to the catheter body 104, for example, through the lumen 128 of the removal device 114 or the lumen 116 of the outer sheath 110, to remove occlusive material, which may be disrupted by the removal device 114 and/or by the reference member 120. The fluid source 136 may deliver lytics or an irrigant, such as saline, through any of the lumens, such as the lumen 128 of the removal device 114, before, during, and/or after activation of the removal device 114 and/or the reference implement 112. Alternatively, lytic agents, such as tPA, may be infused through the removal device 114 when the removal device 114 is a simple lytic drip or other chemical removal device.

The use of the catheter system 10 in removing at least a portion of an occlusion from a body lumen, e.g., the vasculature, will now be described. With reference to the flow chart 200 depicted in FIG. 5, the vasculature is accessed using known techniques (Step 202). The thrombectomy catheter 100 of the catheter system 10 is advanced through the vasculature to a location adjacent a treatment site, e.g., an occlusion (Step 204). The reference implement 112 is moved from the first longitudinal position of FIG. 2 to the second longitudinal position of FIG. 3 to permit at least a portion of the reference member 120 to self expand, engaging the inner wall "w" of the vasculature "v" as depicted in FIG. 6 (Step 206).

In this position, the reference member 120 generally centers the catheter body 104 within the vasculature "v". An image, through, e.g., x-ray imaging, may be taken of the reference member 120 and/or the radiopaque markers 124 within the vasculature "v" with the data corresponding to the length and/or orthogonal (e.g., cross-sectional) dimension of the reference member 120 and/or radiopaque markers 124 associated with the image, which may be recorded in a storage media (Step 208). Thereafter, the removal device 114 is advanced through the outer sheath 110 and the reference shaft 118 with the cutting member 130 extending through the reference member 120 and into the occlusion "O". The drive mechanism 132 is activated causing the cutting member 130 to rotate, vibrate and/or oscillate to disrupt the occlusive material of the occlusion "O" (Step 210). As an option, during, subsequent to, or prior to activation of the drive mechanism 132, the vacuum source 134 may deliver negative pressure to draw the disrupted occlusive particles through the catheter system 10, such as through the lumen 128 of the removal device 114 or the lumen 116 of the outer sheath 110. In addition, as a further option, the fluid source 136 may deliver irrigant solution, drugs, and/or lytics through the catheter body 104 or supply lytics and/or an irrigant through, e.g. the lumen 128, of the removal device 114 or the lumen 116 of the outer sheath 110 (Step 212).

Figure 7:
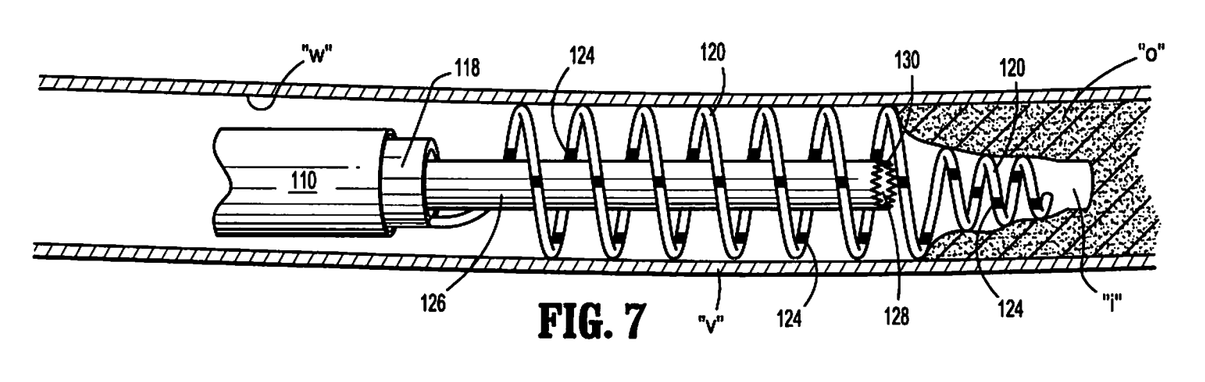
FIG. 7 is a partial cut-away view illustrating the distal end of the thrombectomy catheter of FIG. 2 with the reference member advanced within the occlusion and the removal device at least partially retracted.

Once a volume of occlusive material has been removed from the occlusion "O", the removal device 114 may be retracted through the reference member 120 and at least partially into the reference shaft 118 and/or the outer sheath 110. The reference member 120 is thereafter advanced within the enlarged void "i" formed by the removed material within the occlusion "O" (Step 214). FIG. 7 illustrates retraction of the removal device 114 and advancement of the reference member 120 within the void "i". The reference member 120, due to its inherent resilient characteristics, also will generally conform to the inner boundary defined by the void "i" within the occlusion "O". Once positioned within the void "i", an image is obtained of the reference member 120 and/or the radiopaque markers 124, and may be recorded (Step 216). The resulting image data provides the clinician with an indication of the extent or volume of the void "i" formed by the removal device 114 because of the radiopacity of the reference member 120 and/or the radiopaque markers 124, thereby providing an indication of progress or removal of the occlusion.

Figure 5:
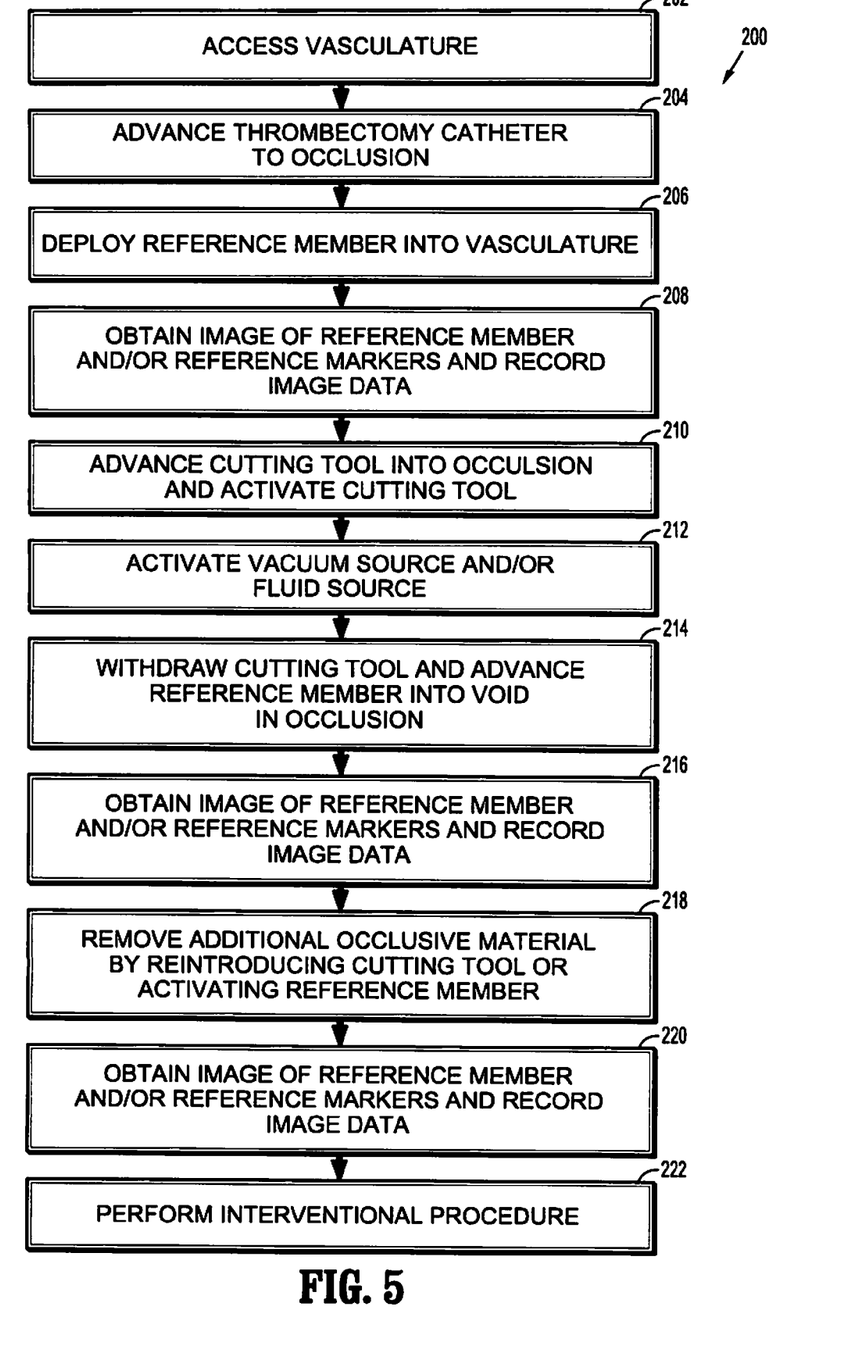
FIG. 5 is a flow chart illustrating use of the thrombectomy catheter system in removing an occlusion.
Figure 6:
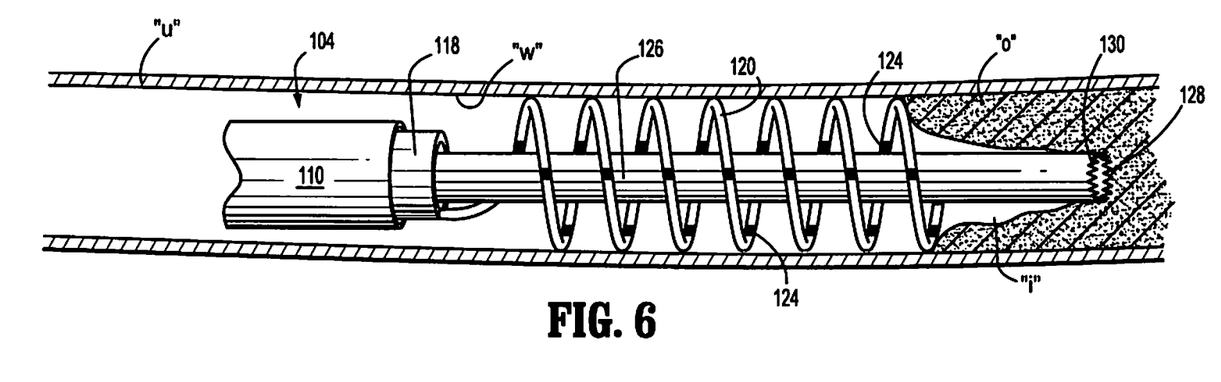
FIG. 6 is a partial cut-away view illustrating the distal end of the thrombectomy catheter of FIG. 2 introduced within a body lumen with the reference member deployed and the removal device disrupting an occlusion.
Figure 8:
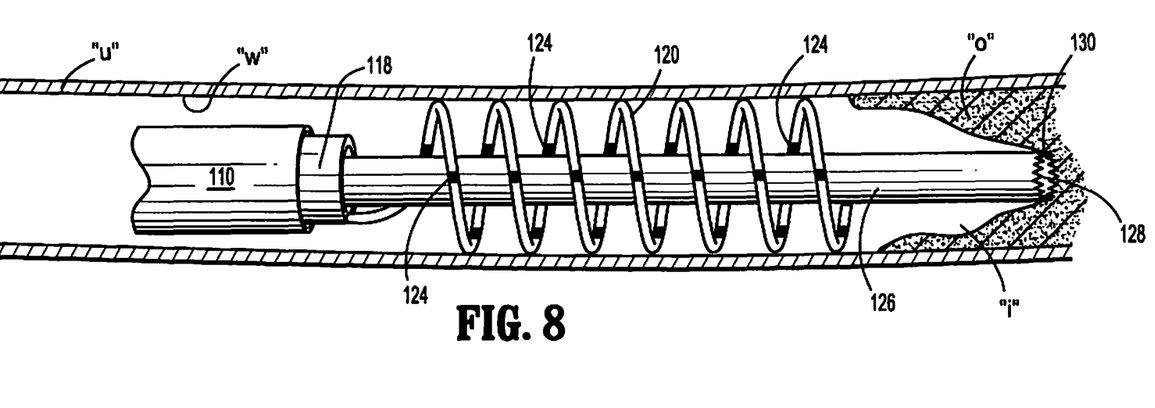
FIG. 8 is a partial cut-away view illustrating the distal end of the thrombectomy catheter of FIG. 2 with the reference member retracted and the removal device advanced within the occlusive material to cut an additional portion of the occlusion.

With reference to FIG. 8, in conjunction with the flow chart of FIG. 5, the procedure may be continued by with-drawing the reference shaft 118 and the reference member 120 from the occlusion "O", and reintroducing the removal device 114 within the occlusion to remove more occlusive material upon actuation of the drive mechanism 132 (Step 218). Additionally or alternatively, the reference member 120 may be utilized to remove occlusive material through activation of the drive mechanism 132 prior to, or subsequent to, reintroducing the removal device 114 within the occlusion.

Figure 9:
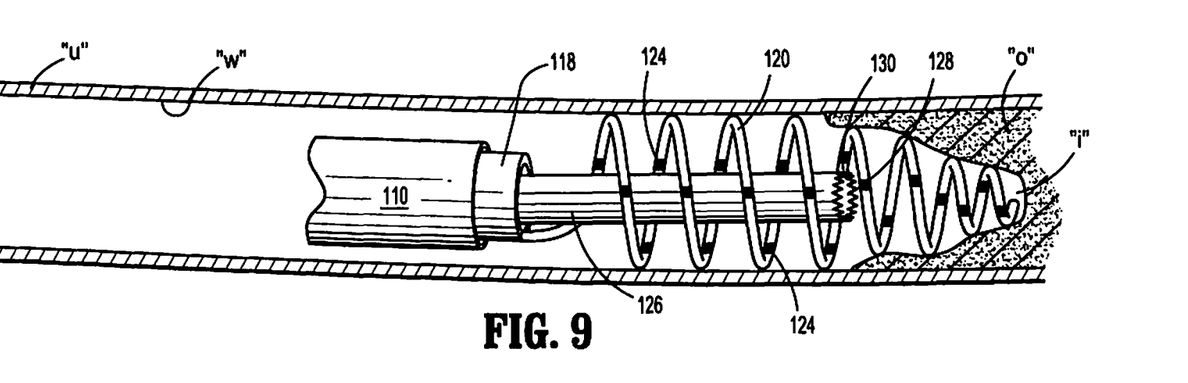
FIG. 9 is a partial cut-away view illustrating the distal end of the thrombectomy catheter of FIG. 2 with the reference member advanced within the occlusion.
Figure 10:
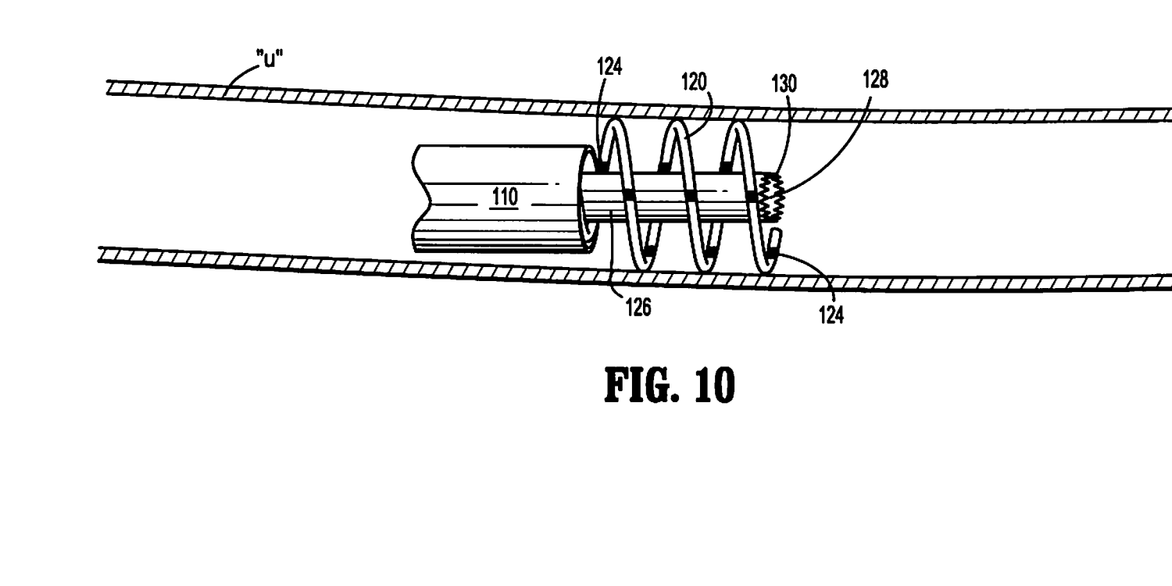
FIG. 10 is a partial cut-away view illustrating the distal end of the thrombectomy catheter of FIG. 2 with the reference member and the removal device being retracted within the outer sheath.

Thereafter, the reference member 120 is advanced in the larger void "i" within the occlusion "O" as depicted in FIG. 9, and an image is taken to ascertain the degree of removal of the occlusive material (Step 220). The reference member 120 will conform to the void "i" and to the vasculature. The process including, e.g., Steps 214-220, may be repeated until the occlusion "O" is sufficiently removed from the vasculature "v". With the occlusion "O" cleared, the reference implement 112 and the removal device 114 may be independently, or simultaneously, extracted within the outer sheath 110 as depicted in FIG. 10 and the thrombectomy catheter removed from the vasculature "v". The reference member 120 will deflect inwardly when drawn into the outer sheath 110 for repositioning within the longitudinal lumen 116 of the outer sheath 110. Follow up interventional procedures may then be performed including application of a stent, angioplasty or other vascular interventional procedures (Step 222).

Figure 11:
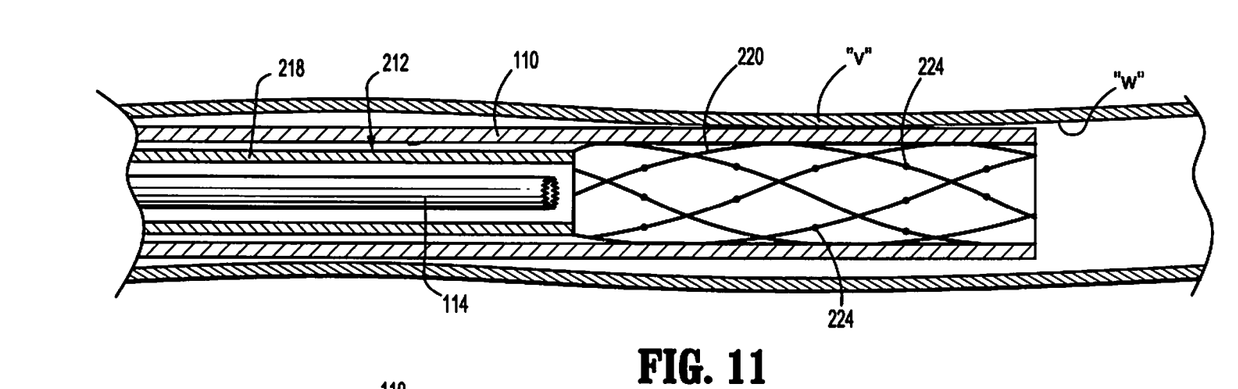
FIG. 11 is a side plan view in partial cross-section of the distal end of another illustrative example of a thrombectomy catheter incorporating an expandable mesh as the reference member with the expandable mesh confined within an outer sheath.
Figure 12:
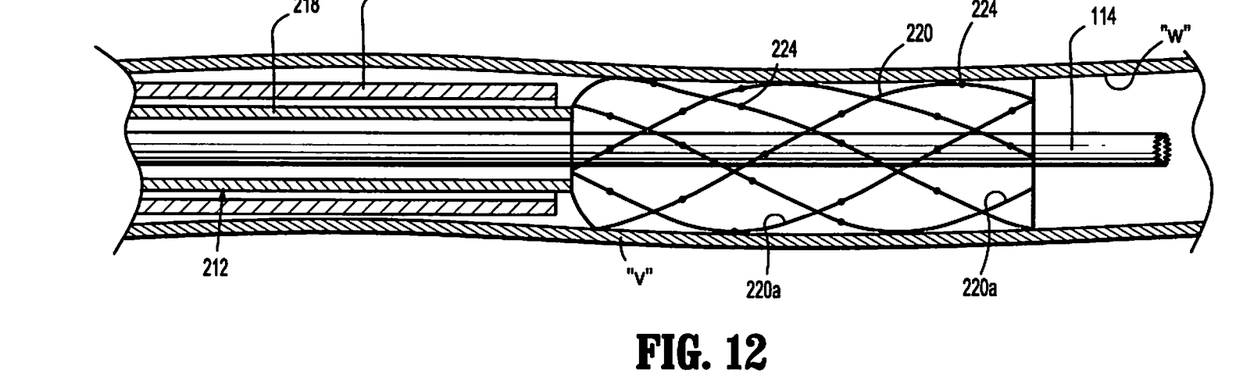
FIG. 12 is a side plan view in partial cross-section illustrating the expandable mesh of FIG. 11 deployed from the outer sheath.

FIGS. 11-12 depict another illustrative example of the reference implement of the thrombectomy catheter 100. The reference implement 212 includes a reference member 220 in the form of a cage, mesh or woven element connected to a reference shaft 218. The reference member 220 is self-expanding and may be fabricated from any of the materials identified hereinabove in connection with the reference member 120 of FIGS. 1-10. The reference member 220 also may include radiopaque markers 224, which may be spaced at predefined intervals (radial and longitudinal) along the reference member 220. The reference member 220 may include sharpened edges 220a to assist in removal of the occlusion. In the first position depicted in FIG. 11, the reference member 220 is confined within the outer sheath 110. Upon movement of the reference member 220 to the second position depicted in FIG. 12, the reference member 220 is exposed from the outer sheath 110 and self-expands to engage the inner wall "w" of the vasculature "v". In embodiments, the outer sheath 110 may be retracted to expose the reference member 220. The reference member 220 may be used in a similar manner to that described in connection with the reference member 120 of FIGS. 1-9, i.e., it may be positionable within the occlusion "O" to occupy a void "i" in the occlusion "O" subsequent to use of the removal device 114, to provide visual or quantitative data through imaging to ascertain progress of removal of the occlusive material or characteristics of the occlusion "O".

Figure 13:
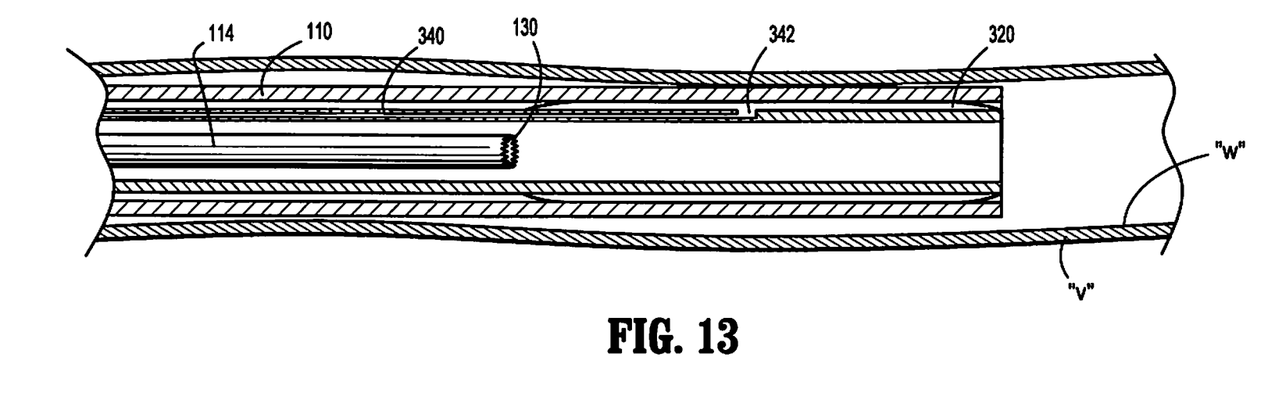
FIG. 13 is a side plan view in partial cross-section of the distal end of yet another illustrative example of a thrombectomy catheter incorporating an inflatable balloon as the reference member with the inflatable balloon confined within the outer sheath.
Figure 14:
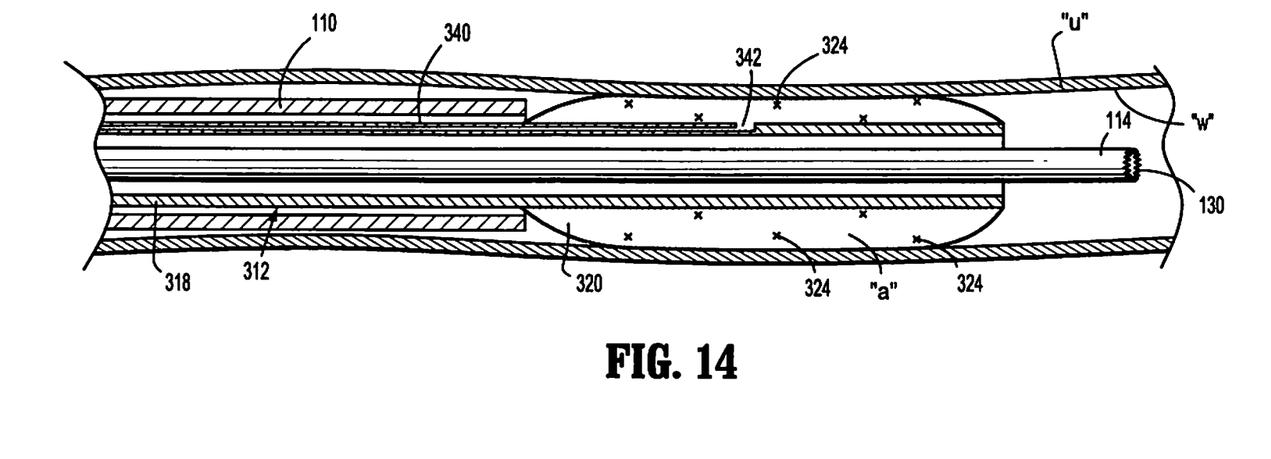
FIG. 14 is a side plan view in partial cross-section illustrating the inflatable balloon of FIG. 13 deployed from the outer sheath and in an inflated condition.

FIGS. 13-14 depict yet another illustrative example of the reference implement 312. The reference implement 312 includes a reference shaft 318 and a reference member 320 in the form of a balloon which is coaxially mounted about the reference shaft 318. The reference member 320 is in fluid communication with inflation media through a lumen 340, which, in one embodiment, extends through the wall of the reference shaft 318. An inflation opening 342 in the reference shaft 318 is in fluid communication with the lumen 340 and the internal volume of the reference member 320 to supply inflation media to the reference member 320. The reference member 320 may also include radiopaque markers 324 at predefined spaced locations on the outer surface of the reference member 320. In the first position, the reference member 320 is confined within the outer sheath 110 as depicted in FIG. 13. Subsequent to relative movement of the reference implement 312 and the outer sheath 110 to the second position depicted in FIG. 14, the reference member 320 is exposed and can be inflated through introduction of inflation media through the lumen 340 and the inflation opening 342 to engage the internal wall "w" of the vasculature "v". The reference member 320 is conformable such that when positioned within a void "i" in the occlusion "O", the reference member 320 will occupy the void "i" to provide visual and/or quantitative data through imaging of the radiopaque markers 324 to ascertain progress of removal of the occlusion. In the alternative, the reference member 320 may be filled with a contrasting agent "a" (FIG. 14) to be detected during imaging.

Figure 15:
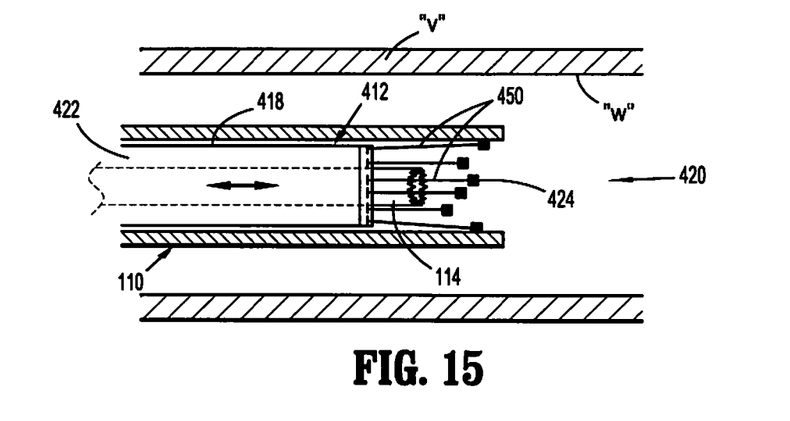
FIG. 15 is a side plan view in partial cross-section of the distal end of still another illustrative example of a thrombectomy catheter incorporating a plurality of fingers as the reference member with the fingers confined within the outer sheath.
Figure 16:
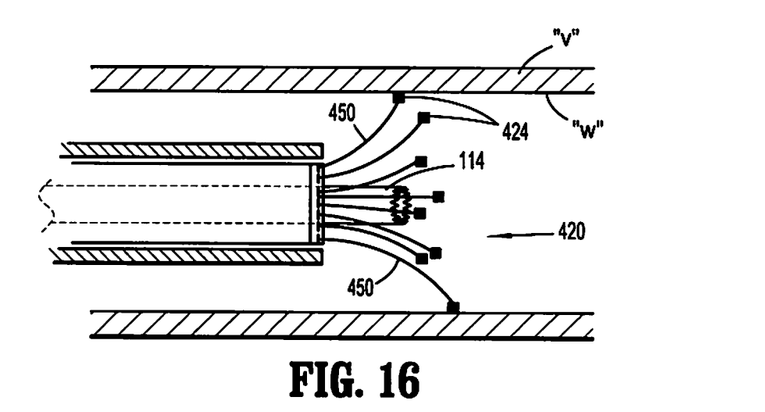
FIG. 16 is a side plan view in partial cross-section illustrating the fingers of FIG. 15 deployed from the outer sheath and in radially expanded condition.
Figure 17:
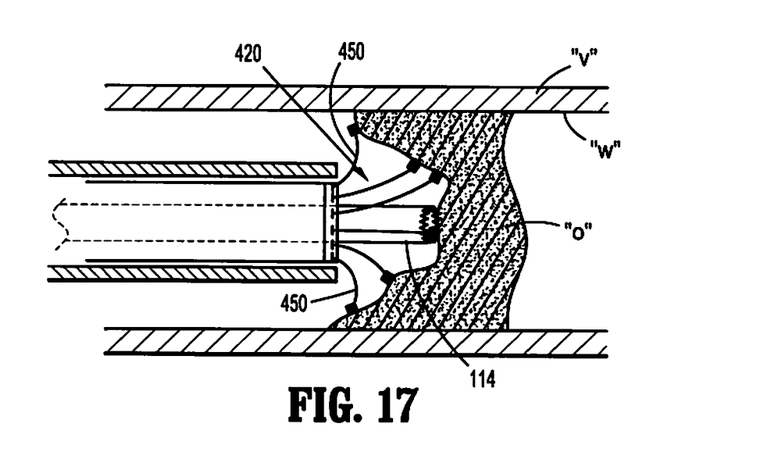
FIG. 17 is a side plan view in partial cross-section illustrating the fingers of FIG. 15 deployed within an occlusion.

FIGS. 15-17 depict a further illustrative example of the reference implement 412. The reference implement 412 includes a reference shaft 418 and reference member 420. The reference member 420 includes a plurality of fingers 450 that extend distally from the reference shaft 418 and are biased radially outward. The reference member 420 is at least partially confined within the outer sheath 110 when in a first position (FIG. 15) and spring radially outward when the reference member 420 is advanced out of the outer sheath 110 (FIG. 16), either by retracting the outer sheath 110 or by advancing the reference implement 412 distally. The reference shaft 418 may also include a longitudinal lumen 422 through which the removal device 114 may pass.

Each finger 450 of the reference member 420 is made of a material that enables each finger 450 to flex while also springing radially outward when exposed from the outer sheath 110. Further, each finger 450 may be made of a radiopaque material. In addition, or alternatively, the fingers 450 may include radiopaque markers 424 along their length. As depicted in FIGS. 15-17, each finger 450 may include a radiopaque marker 424 at its distal end, which will enable a physician to visualize the inner wall "w" of the vasculature "v" as the radiopaque markers 424 engage the inner wall "w" (FIG. 16). Further, each radiopaque marker 424 may be of alternating shapes to enable the physician to better visualize the shape of the vasculature "v", as described above with reference to FIGS. 1-9. Referring to FIG. 17, the reference member 420 may be advanced into a void "i" in an occlusion "o" as the removal device 114 removes portions of the occlusion "o". Because of the independent movement of each finger 450 of the reference member 420, the radiopaque markers 424 may provide a more accurate depiction of the occlusion "o" under x-ray. In other words, because each finger 450 of the reference member 420 is not connected or tied to an adjacent finger 450, each finger 450 of the reference member 420 may penetrate into gaps or irregular voids in the occlusion "o" with less chance of the reference member 420 bridging such gaps or voids.

While six fingers 450 are shown, any number of fingers 450 may be included. The reference implement 412 may be used in the same manner as described above with reference to FIG. 5.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical apparatus comprising:
an elongate outer sheath dimensioned for positioning within a body lumen of a patient adjacent an occlusion, the elongate outer sheath having a proximal end, a distal end, and a longitudinal axis extending between the proximal end and the distal end, and the elongate outer sheath defining a longitudinal lumen along at least a portion of the longitudinal axis;
a reference member configured for longitudinal movement relative to the elongate outer sheath between a first position at least partially disposed within the longitudinal lumen and a second position at least partially exposed from the longitudinal lumen, wherein the reference member expands when in the second position to generally conform to an internal dimension of the body lumen and internal boundaries of the occlusion, the reference member further comprising a radiopaque material configured for visualization of the reference member to assist in determining physical characteristics of at least one of the body lumen or the occlusion when in the second position; and
a removal device distinct from the reference member and configured to move longitudinally with respect to, and radially within, at least a portion of the reference member, wherein the removal device is configured to remove at least a portion of the occlusion within the body lumen, wherein at least a portion of the removal device is extendable distally beyond the distal end of the elongate outer sheath, and wherein a distal end of the reference member is configured to extend distally of a distal end of the removal device.

2. The surgical apparatus according to claim 1 wherein the radiopaque material defines radiopaque markers arranged in a predefined radially and longitudinally spaced configuration.

3. The surgical apparatus according to claim 1 wherein the reference member is dimensioned for positioning at least partially within the occlusion within the body lumen.

4. The surgical apparatus according to claim 1 wherein the reference member is configured for reciprocal longitudinal movement relative to the outer sheath between the first and second positions, the reference member being repositionable to the first position subsequent to movement thereof to the second position.

5. The surgical apparatus according to claim 1 wherein the reference member is configured to assist in centering the removal device within the body lumen.

6. The surgical apparatus according to claim 1 wherein the reference member includes a self-expanding coil.

7. The surgical apparatus according to claim 1 wherein the reference member includes a self-expanding cage or mesh.

8. The surgical apparatus according to claim 1 wherein the reference member includes a balloon.

9. The surgical apparatus according to claim 1 wherein the reference member includes a plurality of fingers biased radially outward.

10. The surgical apparatus according to claim 1 wherein the removal device is configured for reciprocal longitudinal movement relative to the reference member between a retracted position disposed within the reference member and an advanced position distal of the reference member.

11. The surgical apparatus according to claim 1, wherein the removal device comprises a shaft defining a lumen and a cutting member at a distal end of the shaft.

12. The surgical apparatus according to claim 11, wherein the cutting member comprises one or more teeth, serrations, blades, ridges, or edges configured to remove the at least a portion of the occlusion within the body lumen.

13. A surgical apparatus comprising:
an elongate outer sheath dimensioned for positioning within a vasculature of a patient, the elongate outer sheath having a proximal end, a distal end, and a longitudinal axis extending between the proximal end and the distal end, and the elongate outer sheath defining a longitudinal lumen along at least a portion of the longitudinal axis, wherein the outer sheath is advanceable to a location adjacent an occlusion in the vasculature;
a reference member configured for longitudinal movement relative to the elongate outer sheath between a first position at least partially disposed within the longitudinal lumen and a second position at least partially exposed from the longitudinal lumen, wherein the reference member, when in the second position, is dimensioned for at least partial insertion within the occlusion and configured to generally conform to internal boundaries of the occlusion and areas of the vasculature adjacent the occlusion, the reference member further comprising a radiopaque material configured for visualization of the reference member to assist in determining characteristics of at least one of the occlusion and the areas of the vasculature adjacent the occlusion; and
a removal device distinct from the reference member and configured to move longitudinally with respect to, and radially within, at least a portion of the reference member, wherein the removal device is configured to remove at least a portion of the occlusion within the vasculature, wherein at least a portion of the removal device is extendable distally beyond the distal end of the elongate outer sheath, and wherein a distal end of the reference member is configured to extend distally of the distal end of the removal device.

14. A surgical method comprising:
advancing an elongate outer sheath within a body lumen to a location adjacent an occlusion;
deploying a reference member comprising radiopaque material from the elongate outer sheath, wherein the reference member is configured for longitudinal movement relative to the elongate outer sheath between a first position at least partially disposed within the longitudinal lumen and a second position at least partially exposed from the longitudinal lumen, wherein the reference member, when in the second position, is dimensioned for at least partial insertion within the occlusion and capable of generally conforming to internal boundaries of the occlusion and areas of the body lumen adjacent the occlusion, and wherein the radiopaque material is configured for visualization of the reference member to assist in determining physical characteristics of the occlusion and areas of the body lumen adjacent the occlusion when inserted within the occlusion;

expanding the reference member whereby the reference member is at least partially disposed within the occlusion;

visualizing the reference member to ascertain physical characteristics of at least one of the occlusion and the areas of the body lumen adjacent the occlusion;

advancing a removal device relative to the elongate outer sheath, wherein the removal device is distinct from the reference member and configured to move longitudinally with respect to, and radially within, at least a portion of the reference member, wherein the removal device is configured to remove at least a portion of the occlusion within the body lumen, wherein at least a portion of the removal device is extendable distally beyond the distal end of the elongate outer sheath, and wherein a distal end of the reference member is configured to extend distally of a distal end of the removal device; and activating the removal device to remove at least a portion of the occlusion.

15. The surgical method according to claim 14 wherein visualizing the reference member is performed prior to activating the removal device.

16. The surgical method according to claim 15 wherein visualizing the reference member is performed subsequent to activating the removal device to determine progress of the removing of the occlusion.

17. The surgical method according to claim 16 wherein the reference member includes radiopaque markers arranged in a predefined radially- and longitudinally-spaced configuration and wherein visualizing the reference member includes viewing the radiopaque markers to determine the physical characteristics of the occlusion.

18. The surgical method according to claim 14 further comprising retracting the reference member from the occlusion prior to activating the removal device.

19. The surgical method according to claim 14 further comprising advancing the reference member within the occlusion subsequent to activating the removal device, and thereafter visualizing the reference member to ascertain progress of removing the occlusion.

20. The surgical method according to claim 19 further comprising:

retracting the reference member from the occlusion;

advancing the removal device relative to the reference member; and removing additional portions of the occlusion with a cutting member at a distal end of a shaft of the removal device, the shaft defining a lumen.

21. A surgical apparatus comprising:

an elongate outer sheath dimensioned for positioning within a body lumen of a patient adjacent an occlusion, the elongate outer sheath having a proximal end, a distal end, and a longitudinal axis extending between the proximal end and the distal end, and the elongate outer sheath defining a longitudinal lumen along at least a portion of the longitudinal axis;

a reference member configured for longitudinal movement relative to the elongate outer sheath between a first position at least partially disposed within the longitudinal lumen and a second position at least partially exposed from the longitudinal lumen, wherein the reference member expands when in the second position to generally conform to an internal dimension of the body lumen and internal boundaries of the occlusion, the reference member further comprising a radiopaque material configured for visualization of the reference member to assist in determining physical characteristics of at least one of the body lumen or the occlusion when in the second position; and a removal device distinct from the reference member and configured to move longitudinally with respect to, and radially within, at least a portion of the reference member, wherein the removal device comprises a shaft defining a lumen and a cutting member at a distal end of the shaft, the cutting member configured to remove at least a portion of the occlusion within the body lumen, and wherein at least a portion of the removal device is extendable distally beyond the distal end of the elongate outer sheath.

* * * * *